US010343972B2

(12) United States Patent
Igarashi et al.

(10) Patent No.: US 10,343,972 B2
(45) Date of Patent: Jul. 9, 2019

(54) FULLERENE DERIVATIVE, FLUORORESIN COMPOSITION, AND LUBRICANT

(71) Applicant: SHOWA DENKO K.K., Tokyo (JP)

(72) Inventors: Takeshi Igarashi, Tokyo (JP); Kentaro Watanabe, Tokyo (JP)

(73) Assignees: SHOWA DENKO K.K., Tokyo (JP); MITSUBISHI CORPORATION, Tokyo (JP)

( * ) Notice: Subject to any disclaimer, the term of this patent is extended or adjusted under 35 U.S.C. 154(b) by 315 days.

(21) Appl. No.: 15/116,672

(22) PCT Filed: Feb. 20, 2015

(86) PCT No.: PCT/JP2015/054870
§ 371 (c)(1),
(2) Date: Aug. 4, 2016

(87) PCT Pub. No.: WO2015/125940
PCT Pub. Date: Aug. 27, 2015

(65) Prior Publication Data
US 2016/0347703 A1    Dec. 1, 2016

(30) Foreign Application Priority Data

Feb. 21, 2014  (JP) ................. 2014-031919
Aug. 12, 2014  (JP) ................. 2014-164308
Sep. 30, 2014  (JP) ................. 2014-200778

(51) Int. Cl.
C07C 69/65      (2006.01)
C07C 69/753     (2006.01)
C07C 69/76      (2006.01)
C10M 105/54     (2006.01)
C10M 107/38     (2006.01)
C07C 69/88      (2006.01)

(52) U.S. Cl.
CPC ............ C07C 69/65 (2013.01); C07C 69/753 (2013.01); C07C 69/76 (2013.01); C07C 69/88 (2013.01); C10M 105/54 (2013.01); C10M 107/38 (2013.01); C07C 2604/00 (2017.05); C10M 2211/0425 (2013.01); C10M 2213/043 (2013.01); C10N 2230/06 (2013.01); C10N 2240/204 (2013.01); C10N 2250/121 (2013.01)

(58) Field of Classification Search
CPC ......... C07C 69/65; C07C 69/88; C07C 69/76; C07C 69/753; C07C 2104/00; C10M 107/38; C10M 105/54; C10M 2213/043; C10M 2211/0425; C10N 2250/121; C10N 2240/204; C10N 2230/06
See application file for complete search history.

(56) References Cited

U.S. PATENT DOCUMENTS 5,382,718 A  *  1/1995  Bekiarian ............... C07C 23/46
                                                          558/388
2015/0162044 A1    6/2015  Hanawa et al.
2015/0199988 A1    7/2015  Hanawa et al.

FOREIGN PATENT DOCUMENTS

| JP | 8-49116 A | 2/1996 |
| JP | 10-310709 A | 11/1998 |
| JP | 2006-117760 A | 5/2006 |
| JP | 2006-131874 A | 5/2006 |
| JP | 2006131874 A * | 5/2006 ............ B82Y 30/00 |
| JP | 2013-140923 A | 7/2013 |
| JP | 2013-170137 A | 9/2013 |
| JP | 5600202 B1 | 10/2014 |
| JP | 5600222 B1 | 10/2014 |

OTHER PUBLICATIONS

Bharat Bhushan et al., "Sublimed $C_{60}$ films for tribology", Appl. Phys. Lett., Jun. 21, 1993, pp. 3253-3255, vol. 62, No. 25.
B.M. Ginzburg et al., "Antiwear Effect of Fullerene $C_{60}$ Additives to Lubricating Oils", Russian Journal of Applied Chemistry, 2002, pp. 1330-1335, vol. 75, No. 8.
International Search Report for PCT/JP2015/054870 dated Apr. 21, 2015.
Communication dated Jul. 12, 2017, from the European Patent Office in counterpart European Application No. 15752828.2.

* cited by examiner

Primary Examiner — Taiwo Oladapo
(74) Attorney, Agent, or Firm — Sughrue Mion, PLLC

(57) ABSTRACT

A fullerene derivative of the present invention has a fullerene skeleton and a plurality of perfluoropolyether chains in a molecule, wherein the perfluoropolyether chains are bonded to the fullerene skeleton via methano groups, and a lubricant and fluororesin composition of the present invention contain the derivative.

8 Claims, No Drawings

FULLERENE DERIVATIVE, FLUORORESIN COMPOSITION, AND LUBRICANT

CROSS REFERENCE TO RELATED APPLICATIONS

This application is a National Stage of International Application No. PCT/JP2015/054870 filed Feb. 20, 2015 (claiming priority based on Japanese Patent Application Nos. 2014-031919 filed Feb. 21, 2014, 2014-164308 filed Aug. 12, 2014, and 2014-200778 filed Sep. 30, 2014), the contents of which are incorporated herein by reference in their entirety.

TECHNICAL FIELD

The present invention relates to a fullerene derivative, a fluororesin composition and a lubricant. Priority is claimed on Japanese Patent Application No. 2014-031919, filed Feb. 21, 2014, Japanese Patent Application No. 2014-164308, filed Aug. 12, 2014, and Japanese Patent Application No. 2014-200778, filed Sep. 30, 2014, the contents of which are incorporated herein by reference.

The present invention relates to a fullerene derivative having a fullerene skeleton and a perfluoropolyether (PFPE) chain, and a lubricant and fluororesin composition that contain the fullerene derivative.

BACKGROUND ART

Perfluoropolyether (PFPE) compounds are excellent in heat resistance, chemical resistance, and oxidation resistance. In addition, since perfluoropolyether compounds have a large viscosity index, changes in fluidity (viscosity) are also small in a wide temperature range from low temperatures to high temperatures. Therefore, perfluoropolyether compounds exhibit favorable lubricity. Moreover, perfluoropolyether compounds are incombustible and have almost no adverse effects on the polymer-based materials such as rubbers, plastics, and the like. Furthermore, perfluoropolyether compounds also have properties such as low vapor pressure and low evaporation loss, low surface tension, and high electrical insulating properties. Therefore, perfluoropolyether compounds are known to exhibit high performance over an extremely wide range as lubricants. For this reason, they are widely used in the vacuum pump oil and the lubrication of a magnetic disk/tape or the like as a lubricating oil, a heating medium, a non-pressure-sensitive adhesive and other applications. Since perfluoropolyether compounds are excellent in heat resistance, chemical resistance and oxidation resistance, they can also be used in special applications such as the packing rubbers in chemical plants as fluorine resins, such as perfluoroelastomers, fluororubbers, PTFE, and PFA. Because such fluororesins are used in very harsh conditions, further improvements of heat resistance in particular have been required.

On the other hand, C60 which is a type of fullerene has been known to be useful as a lubricant. In Non-Patent Document 1 (Bhushan et al.: Appl. Phys. Lett. 62, 3253 (1993)), the reduction of the friction coefficient has been confirmed in a silicon substrate where a vapor-deposited film of C60 has been formed. In Non-Patent Document 1, a fullerene derivative obtained by introducing a perfluoropolyether group into a fullerene has also been proposed. However, there is no description with regard to specific compounds or their production method.

Moreover, C60 is known to exhibit excellent properties as an additive to conventional lubricating oils. In Non-Patent Document 2 (Ginzburg et al.: Russian Journal of Applied Chemistry 75, 1330 (2002)), the frictional resistances of those obtained by applying an ordinary lubricating oil onto the surface of a copper foil and those obtained by applying the oil added with 5% of C60 have been measured. The frictional resistance was measured by rubbing a steel roller while applying a load. As a result, it has been confirmed that the abrasion resistance improves when C60 is added, as compared with the case where no addition was made.

In Patent Document 1 (Japanese Unexamined Patent Application, First Publication No. 2006-131874), a lubricant composed of a mixture of C60, a C60 derivative having a carboxyl group, a hydroxylated fullerene or a fullerene derivative having an ester group, and a perfluoropolyether has been described.

In addition to this, fullerene derivatives have been used in various fields. In Patent Document 2 (Japanese Unexamined Patent Application, First Publication No. 2013-140923) and Patent Document 3 (Japanese Unexamined Patent Application, First Publication No. 2013-170137), a fullerene derivative having one perfluoropolyether group in the molecule as an n-type semiconductor material has been described.

In Patent Document 4 (Japanese Unexamined Patent Application, First Publication No. Hei 10-310709), a crystalline thermoplastic resin composition obtained by adding 0.1 to 2,000 ppm of carbon cluster (fullerene) with respect to a crystalline thermoplastic resin has been disclosed. The crystalline thermoplastic resin composition has a high crystallization rate, so that excellent properties of the crystalline thermoplastic resin are not impaired. In addition, mechanical properties and in particular, the molding cycle is favorable.

In Patent Document 5 (Japanese Unexamined Patent Application, First Publication No. Hei 8-49116), fibers, films or hollow bodies that contain a polyester and fullerene and have an individual fiber titer of less than 10 dtex have been disclosed.

In Patent Document 6 (Japanese Unexamined Patent Application, First Publication No. 2006-117760), a polyester-based resin composition in which fullerenes are dispersed on the order of nanometers has been disclosed. The dispersion of fullerenes has been realized by producing the polyester resin composition using a fullerene solution.

CITATION LIST

Patent Documents

[Patent Document 1] Japanese Unexamined Patent Application, First Publication No. 2006-131874
[Patent Document 2] Japanese Unexamined Patent Application, First Publication No. 2013-140923
[Patent Document 3] Japanese Unexamined Patent Application, First Publication No. 2013-170137
[Patent Document 4] Japanese Unexamined Patent Application, First Publication No. Hei 10-310709
[Patent Document 5] Japanese Unexamined Patent Application, First Publication No. Hei 8-49116
[Patent Document 6] Japanese Unexamined Patent Application, First Publication No. 2006-117760

Non-Patent Documents

[Non-Patent Document 1] Appl. Phys. Lett. 62, 3253 (1993)
[Non-Patent Document 2] Russian Journal of Applied Chemistry 75, 1330 (2002)

SUMMARY OF INVENTION

Technical Problem

When a compound having a fullerene skeleton is used as a lubricant, the fullerene itself aggregates. Therefore, favorable dispersibility of the compound having a fullerene skeleton cannot be achieved, and the lubricant cannot impart sufficient wear resistance to the target object. In Patent Document 1, the use of a mixture composed of a fullerene, a fullerene derivative and a perfluoropolyether as a lubricant has been described. However, the fullerene and the fullerene derivative described in Patent Document 1 do not exhibit sufficient affinity with the perfluoropolyether and tend to aggregate, which is a problem. Therefore, there is a problem with the fullerene and the fullerene derivative described in Patent Document 1 that it is impossible to impart sufficient wear resistance to the target object even if used as a lubricant simultaneously with the perfluoropolyether.

When using a fullerene as an additive to a fluororesin, fullerenes such as C60 are poorly soluble in fluororesins. For this reason, it is difficult to uniformly disperse a fullerene. Therefore, it has not been possible to sufficiently achieve the effect of improving the thermal properties by fullerenes.

The present invention has been made in view of the above circumstances, with an object of providing a fullerene derivative having a fullerene skeleton and a plurality of perfluoropolyether chains in a molecule, and the application thereof. As this application, for example, lubricants containing the fullerene derivative and exhibiting excellent wear resistance, and fluororesin compositions containing the fullerene derivative and exhibiting excellent thermal resistance and the like can be mentioned.

Solution to Problem

The inventors of the present invention have found that a lubricant containing a fullerene derivative having a fullerene skeleton and a plurality of perfluoropolyether chains in a molecule is excellent in improving the wear resistance of the target object. In addition, it was found that a fluororesin composition containing the fullerene derivative exhibits excellent thermal resistance.

In other words, the present invention includes the following configurations.

[1] A fullerene derivative including, in a molecule, a fullerene skeleton and a plurality of perfluoropolyether chains linked to the fullerene skeleton via a carbon atom bonded to the fullerene skeleton at two locations.

[2] The fullerene derivative according to [1] including 2 to 5 perfluoropolyether chains linked to the fullerene skeleton.

[3] The fullerene derivative according to [1] or [2], wherein the fullerene derivative is a compound represented by the following general formula (1):
(in the formula, FLN represents a fullerene skeleton, A represents a group having a perfluoropolyether chain, $R^1$ represents an organic group having 1 to 24 carbon atoms, m is an integer of 0 to 5, and n is an integer of 2 to 5).

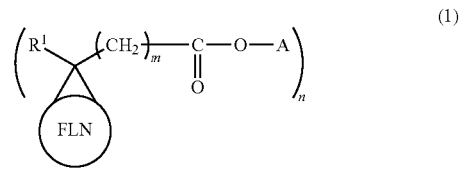

[4] The fullerene derivative according to [3], wherein the $R^1$ is an aryl group.

[5] The fullerene derivative according to any one of [1] to [4], wherein the fullerene skeleton is C60.

[6] The fullerene derivative according to any one of [1] to [5], wherein the perfluoroether chains have at least one partial structure selected from the group consisting of $-(CF_2O)_x-$, $-(CF_2CF_2O)_x-$, $-(CF_2CF_2CF_2O)_x-$, $-(CF_2CF_2CF_2CF_2O)_x-$, and $-(CF_2(CF_2)_3CF_2O)_x-$: (with the proviso that in the formula, x is an integer of 1 to 50).

[7] The fullerene derivative according to any one of [1] to [6], wherein the perfluoroether chains have a partial structure represented by $-(CF_2CF_2O)_y(CF_2O)_z-$: (with the proviso that in the formula, y and z are integers of 1 to 50).

[8] A fluororesin composition containing the fullerene derivative according to any one of [1] to [7].

[9] A lubricant containing the fullerene derivative according to any one of [1] to [7].

[10] The lubricant according to [9], further including a perfluoropolyether compound having no fullerene skeleton.

Advantageous Effects of Invention

By using a fullerene derivative having a fullerene skeleton and a plurality of perfluoropolyether chains in the molecule, a lubricant excellent in wear resistance can be obtained. In addition, by using a fullerene derivative having a fullerene skeleton and a plurality of perfluoropolyether chains in the molecule, a fluororesin composition excellent in thermal resistance can be obtained.

DESCRIPTION OF EMBODIMENTS

For an embodiment of the present invention, the configuration thereof will be described below. The present invention can be implemented with appropriate modifications within a range that does not change the gist thereof.

A fullerene derivative of the present invention includes, in the molecule, a fullerene skeleton and a plurality of perfluoropolyether chains linked to the fullerene skeleton via a carbon atom bonded to the fullerene skeleton at two locations.

The perfluoropolyether chain reacts with a methano group formed by the cleavage of the double bond of the fullerene skeleton, and is linked to the fullerene skeleton at two locations. In other words, the perfluoroether chain can be said to be bonded with the fullerene skeleton via a methano group.

Since the perfluoroether chain is bonded to the fullerene skeleton at two locations, it is possible to stably maintain the coupling between the perfluoropolyether chain and the fullerene skeleton even under conditions of being exposed locally to high frictional heat and shear force.

The fullerene derivative preferably includes those in which 2 to 5 perfluoropolyether chains are bonded to one fullerene skeleton. If the number of the bonding perfluoroether chains is within this range, the proportion of the perfluoropolyether chain site with respect to the fullerene site in the molecule is considered to be appropriate. Therefore, it becomes particularly easy to achieve the lubricating property of the fullerene derivative and the dispersibility of the fullerene derivative into a fluororesin. In addition, favorable dispersibility of the fullerene derivative with respect to the coated surface can also be achieved.

A typical fullerene is a solid at normal temperatures. For this reason, fullerenes are difficult to dissolve in solvents and aggregate with each other. Therefore, it is difficult to uniformly apply a fullerene onto the coated surface even when added to a lubricant. However, by having a plurality of perfluoropolyether chains, the fullerene derivative of the present invention becomes soluble, for example, in fluorine-based solvents. When the fullerene derivative is made into a solution using this solvent, it is possible to suppress aggregation of the fullerene compound itself. Therefore, when applying a material obtained by adding the solution to the lubricant onto the coated surface, it becomes possible to uniformly apply the fullerene compound to the coated surface.

The perfluoropolyether chain preferably has a partial structure represented by at least one selected from $-(CF_2O)_x-$, $-(CF_2CF_2O)_x-$, $-(CF_2CF_2CF_2O)_x-$, $-(CF_2CF_2CF_2CF_2O)_x-$, and $-(CF_2(CF_2)_3CF_2O)_x-$. Here, x is an integer of 1 to 50, preferably from 2 to 30, and more preferably from 5 to 20. By having these partial structures, the perfluoroether chain increases the solubility in the fluorine-based solvents, with respect to the compounds without these partial structures. As a result, the resultant can be applied onto the coated surface more uniformly.

Among the numerous perfluoroether chains, the perfluoropolyether chains having these partial structures have been produced industrially. For this reason, those having the perfluoropolyether chain can be easily obtained and have high industrial applicability.

Furthermore, it is more preferable that the perfluoroether chain have a partial structure represented by $-(CF_2CF_2O)_y(CF_2O)_z-$. Here, y and z are integers of 1 to 50.

When this structure is included, the proportion of ether sites in the perfluoropolyether chain is substantially increased. For this reason, the flexibility of the perfluoropolyether chain is expected to increase. As a result, lubricity and solubility in fluororesins are improved.

In the fullerene derivative of the present invention, the binding positions are arbitrary when two or more carbon atoms are newly bonded to the fullerene skeleton. Among them, the newly bound carbon atoms are preferably bonded to the symmetrical positions with respect to the center of the fullerene skeleton in view of increasing the structural stability of the resulting compound.

The fullerene derivative of the present invention is preferably a compound having a fullerene skeleton represented by the general formula (1). In the formula, FLN represents a fullerene skeleton, and A represents a group having the perfluoropolyether chain. Further, in the formula, $R^1$ represents an organic group of 1 to 24 carbon atoms, m is an integer of 0 to 5, and n is an integer of 2 to 5.

In the compound having a fullerene skeleton represented by the general formula (1), n (n is an integer of 2 to 4) double bonds in the fullerene skeleton are cleaved, and a new carbon atom binds to each locations through a single bond. An organic group of 1 to 24 carbon atoms represented by $R^1$ and a group represented by $-(CH_2)_m-CO-O-A$ are each bonded to these new carbon atoms through a single bond.

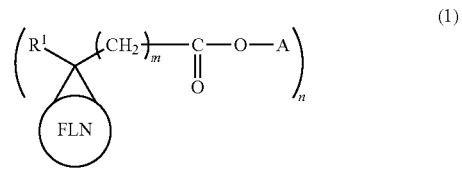

$R^1$ in the general formula (1) is composed of an organic group having 1 to 24 carbon atoms. The organic group is preferably an aryl group, more preferably an aryl group of 6 to 14 carbon atoms, and particularly preferably a phenyl group.

When $R^1$ is an aryl group, a reaction for introducing a substituent group into a fullerene can be easily conducted, and the yield of the desired product is also increased. Therefore, it is possible to inexpensively produce a compound in which a substituent group has been introduced into a fullerene. In particular, since raw materials are easily available, the compound with a phenyl group can be produced more cheaply.

Each of A, $R^1$ and m at n locations in the compound represented by the general formula (1) may be the same or may be different.

In the general formula (1), m is an integer of 0 to 5. If m is in this range, it is preferable because the reaction raw materials are readily available industrially, m is more preferably from 1 to 4, and it is even more preferable if m=3. n is an integer of 2 to 5. n is more preferably from 2 to 4, and it is even more preferable if n=2.

The fullerene derivative of the present invention is also preferably a compound having a fullerene skeleton represented by the following general formula (1B). In the general formula (1B), FLN represents a fullerene skeleton, A represents a group having the perfluoropolyether chain described earlier, $Ar^1$ and $Ar^2$ represent arylene groups of 4 to 18 carbon atoms that may contain a heteroatom, L represents a single bond or an alkylene group of 1 to 5 carbon atoms, x and y are integers of 0 to 3, and n is an integer of 1 to 4, provided that $(x+y) \times n$ is 2 or more. In addition, each of A, $Ar^1$, $Ar^2$ and L at a plurality of locations in the compound represented by the general formula (1B) may be the same or may be different.

At this time, in the compound having a fullerene skeleton represented by the general formula (1B), n (n is an integer of 1 to 4) double bonds in the fullerene skeleton are cleaved, and a new carbon atom binds to each locations through a single bond. Each of these new carbon atoms has a structure in which a group represented by $-Ar^1-(L-CO-O-A)_x$ and a group represented by $-Ar^2-(L-CO-O-A)_y$ are bonded through a single bond.

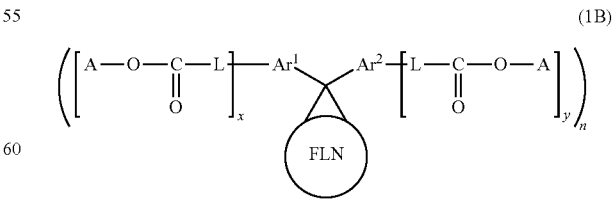

$Ar^1$ and $Ar^2$ are preferably an aromatic hydrocarbon group such as a phenylene group, a naphthalene group, an anthracene group, and a phenanthrene group, or a heterocyclic aryl group containing a hetero atom such as a pyrrole group, a furan group, a thiophene group, an indole group, a benzofuran group, a benzothiophene group, a carbazole group, a dibenzofuran group, a dibenzothiophene group, a phenazine group, a phenoxazine group, and a phenothiazine structure, more preferably an aromatic hydrocarbon group, and particularly preferably a phenylene group.

When $Ar^1$ and $Ar^2$ are arylene groups, a reaction for introducing a substituent group into the fullerene can be easily conducted, and the yield of the desired product is also increased. Therefore, it is possible to inexpensively produce a compound in which a substituent group has been introduced into a fullerene. In addition, among the various possibilities, since raw materials are easily available, the compound with a phenyl group can be produced more cheaply.

L in the general formula (1B) is a single bond or an alkylene group having 1 to 5 carbon atoms. Examples of the alkylene group having 1 to 5 carbon atoms include linear alkylene groups such as $-CH_2-$, $-CH_2CH_2-$, $-CH_2CH_2CH_2-$, $-CH_2CH_2CH_2CH_2-$, and $-CH_2CH_2CH_2CH_2CH_2-$, and alkylene groups having a branched structure such as $-CH(CH_3)-$ and $-CH(CH_3)CH_2-$. L may be appropriately selected in view of ease of availability of raw materials and ease of synthesis.

In the general formula (1B), x and y are integers of 0 to 3. If x and y are within this range, it is preferable because the reaction raw materials are readily available industrially. x and y satisfy the relationship of (x+y)×n being an integer of 2 or more. (x+y)×n is preferably from 2 to 6, and more preferably from 2 to 4.

The fullerene derivative of the present invention is also preferably a compound having a fullerene skeleton represented by the general formula (1C). In the formula, FLN represents a fullerene skeleton, A represents a group having a perfluoropolyether chain, and n represents an integer of 1 to 4. In the formula (1C), the two As may be the same or may be different.

At this time, in the compound having a fullerene skeleton represented by the general formula (1C), n (n is an integer of 1 to 4) double bonds in the fullerene skeleton are cleaved, and a new carbon atom binds to each locations through a single bond. These new carbon atoms has a structure in which two groups represented by $-CO-O-A$ are bonded through single bonds.

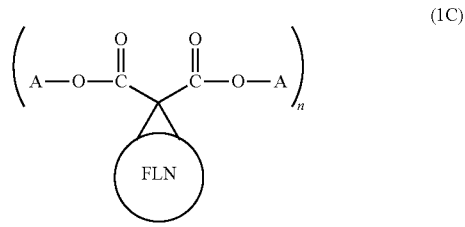

(1C)

In the general formula (1C), n is more preferably from 1 to 2, and it is even more preferable if n=1.

For the fullerene skeleton in the fullerene derivative of the present invention, C60, C70, C76, C78, or the like can be used. In particular, C60 is preferred as the fullerene skeleton in the fullerene derivative. This is because it is possible to easily obtain C60 of high purity, compared to other fullerene skeletons.

(Lubricant)

A lubricant of the present invention contains the fullerene derivative of the present invention. Furthermore, in addition to the fullerene derivative of the present invention, a perfluoropolyether compound having no fullerene skeleton may be included at the same time. The fullerene derivative of the present invention has a perfluoroether chain in the molecule. Therefore, the fullerene derivative has high affinity with perfluoropolyethers, and can be uniformly dispersed in the lubricant.

The content of the fullerene derivative of the present invention in the lubricant is preferably equal to or greater than 0.1%, and more preferably equal to or greater than 1%. By ensuring that the content of the fullerene derivative of the present invention in the lubricant is equal to or greater than 0.1%, the exhibition of wear resistance can be expected. In addition, by ensuring that the content of the fullerene derivative of the present invention in the lubricant is equal to or greater than 1%, it can be expected to achieve an even higher level of wear resistance.

This type of lubricant according to the present invention can be used particularly preferably as a lubricant for magnetic recording media such as magnetic disks.

(Production Method of Lubricant)

The lubricant of the present invention can be produced by the following production method or the production method in accordance therewith, and can be obtained by allowing a condensation reaction or an ester exchange reaction between a fullerene derivative represented by the following general formula (2), (2B) or (2C) and an alcohol represented by A-OH (A represents a group having a perfluoropolyether chain, and is the same as that shown by the general formula (1)).

$R^1$ in the general formula (2) is an organic group having 1 to 24 carbon atoms, m is an integer of 0 to 5, and n is an integer of 2 to 5. $Ar^1$, $Ar^2$, L, x, y, and n in the general formula (2B) are the same as those symbols in the general formula (1B). In the general formula (2C), n is the same as n in the general formula (1C).

B in the general formulae (2), (2B) and (2C) is a hydrogen atom or a hydrocarbon group. This B is preferably a methyl group from the viewpoint of the ease of manufacture. A plurality of B in the compounds represented by the general formula (2), (2B) or (2C) may be the same or different from each other.

The reaction is a condensation reaction in the case where B is a hydrogen atom, and the reaction is an ester exchange reaction in the case where B is a hydrocarbon group.

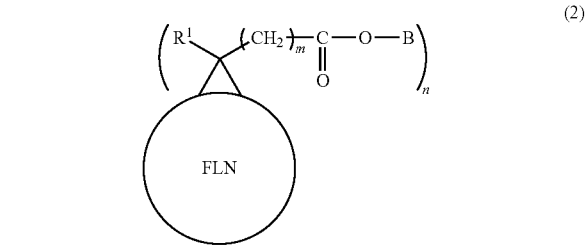

(2)

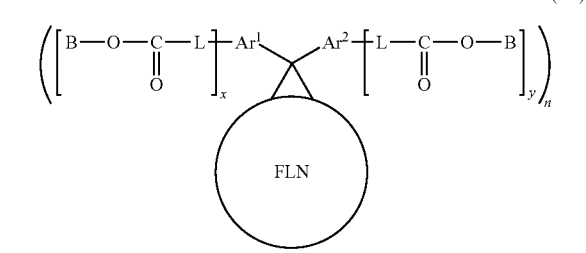

(2B)

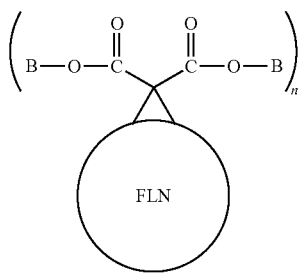

(2C)

If the reaction is a condensation reaction, it is preferable to use a condensing agent. As the condensing agent, any of the typically known condensing agents can be used without limitation. For example, dicyclohexylcarbodiimide and the like can be used as the condensing agent.

If the reaction is an ester exchange reaction, it is preferable to use an acid catalyst or an alkali catalyst. As the acid catalyst or the alkali catalyst, any of the typically known acid catalysts or alkali catalysts can be used without limitation. As the acid catalyst, for example, acetic acid, hydrochloric acid, sulfuric acid, phosphoric acid, p-toluenesulfonic acid, trifluoromethanesulfonic acid, Nation resins, strongly acidic ion-exchange resins, zeolites, and the like can be mentioned. As the alkali catalyst, sodium methoxide, sodium t-butoxide, potassium t-butoxide, sodium hydride, triethylamine, 1,8-diazabicyclo[5.4.0]-7-undecene, and the like can be used.

This reaction can be carried out without a solvent or in a solvent. As the solvent, for example, hexafluorobenzene can be used, although there is no particular limitation as long as the solvent is capable of dissolving the fullerene derivative represented by the general formula (2), (2B) or (2C) and the alcohol represented by A-OH. Further, it is also possible to use a mixed solvent. As the mixed solvent, for example, a mixed solvent of an aromatic solvent, such as toluene, xylene, trimethylbenzene and ortho-dichlorobenzene, and a fluorine-based solvent, such as hexafluorobenzene and 1,1-dichloro-1,2,2,3,3-pentafluoropropane (HCFC-225), and the like can be mentioned.

This reaction is preferably carried out with heating and stirring in an inert gas atmosphere. By performing the reaction in an inert gas atmosphere, it is possible to suppress the production of impurities. The heating is preferably carried out at 40° C. or more and not more than 200° C. If the heating temperature is within this range, a sufficient reaction rate can be achieved, and it is possible to avoid the prolonged reaction time. In addition, it is also possible to avoid an excessive increase in the side reactions and a reduction of the yield.

Then, a crude product is obtained by removing the by-products derived from the condensing agent, the catalysts and the like from the reaction products after the reaction. For example, when using a homogeneous acid catalyst, such as p-toluenesulfonic acid, separation and washing are sequentially performed using ammonia water and purified water, and then the solvent is evaporated to obtain the crude product.

The crude product can be used as it is as a lubricant. If a higher purity is required, for example, the crude product can be further purified by carbon dioxide supercritical fluid extraction. In other words, by placing the crude product in a pressure vessel and allowing the liquid carbon dioxide to flow into the vessel while maintaining the pressure and the temperature in the container, it is possible to bring the carbon dioxide into a supercritical fluid state and to obtain the intended compound by extraction.

The temperature inside the vessel is preferably equal to or more than 31° C. and equal to or less than 80° C. If the temperature inside the vessel is within this range, it is possible to bring carbon dioxide into a supercritical fluid state in a satisfactory manner. Further, the extracting power of the carbon dioxide in a supercritical fluid state would not be weakened. It is preferable that the pressure in the vessel is equal to or more than 7.38 MPa and equal to or less than 30 MPa. If the pressure inside the vessel is within this range, it is possible to bring carbon dioxide into a supercritical fluid state in a satisfactory manner. Further, apparatuses having a general-purpose pressure resistance property can also be used without increasing the apparatus cost. In other words, it is possible to avoid an increase in the production cost.

(Fluororesin Composition)

A fluororesin composition of the present invention contains the fullerene derivative of the present invention. The term "fluororesin" used in the present invention is a general term referring to the polymers containing a fluorine atom such as fully fluorinated polymers, partially fluorinated polymers, and fluorinated resin copolymers. The fullerene derivative of the present invention has a perfluoroether chain in the molecule. Therefore, it has high affinity with fluororesins, and can be uniformly dispersed in fluororesins.

The content of the fullerene derivative of the present invention in the fluororesin is preferably from 0.03% by mass to 3% by mass. By ensuring that the content of the fullerene derivative of the present invention in the fluororesin is within this range, an improvement in the thermal resistance can be expected at an economical cost. In addition, the lower limit of the content is more preferably at least 0.1% by mass, and still more preferably at least 0.3% by mass. If the lower limit of the content is within this range, an even further improvement in the thermal resistance can be expected.

(Production Method of Fluororesin Composition)

The fluororesin composition of the present invention can be obtained, for example, by the following procedure. First, a fluorine resin is swollen and dissolved in a fluorine-based solvent or the like, and the fullerene derivative of the present invention (for example, a compound of the formula 1, or the like) is added thereto. From the resultant obtained by adding the fullerene derivative to the solvent, the solvent was removed by evaporation, followed by drying.

EXAMPLES

As follows is a more detailed description of the present invention based on a series of examples, although the technical scope of the present invention is in no way limited by these examples.

(NMR Analysis)

$^1$H-NMR and $^{13}$C-NMR were measured under the following conditions.

Apparatus: Biospin Avance-500, manufactured by Bruker Corporation.

Sample preparation: a sample (about 10 mg to 30 mg) was dissolved in a $CDCl_3$/hexafluorobenzene mixed solvent (about 0.5 ml). The resultant was then placed in an NMR sample tube having a diameter of 5 mm.

Measurement temperature: room temperature

Reference material: the solvent signal was used as a reference.

(Film Thickness Measurement of Lubricant Coating Film)

The film thickness of the lubricant coating film was determined from the intensity of the absorption peak corresponding to the stretching vibration energy of C—F bond in the infrared absorption spectrum. Measurements were made at 4 points for each lubricant coating film, and the average value was used as the average film thickness of the lubricant coating film.

Apparatus: Nicolet iS50, manufactured by Thermo Fisher Scientific Inc.

Measuring method: reflection absorption spectroscopy.

(Wear Resistance)

The wear resistance of the surface of the lubricant coating film was measured using a pin-on-disk type friction and abrasion tester (FRICTION PLAYER FPR-2000 manufactured by RHESCA Co., Ltd.). Using a sphere made of AlTiC with a diameter of 2 mm as a contact, the test was conducted with a load of 40 gf at a sliding speed of 0.25 m/s. When the abrasion of the lubricant takes place and the lubricant film is eliminated, the contact and the substrate come into direct contact with each other. Therefore, the friction coefficient of the surface of the lubricant coating film varies greatly. As an indicator of the wear resistance, the time until the friction coefficient varied rapidly was measured. Measurements were made 4 times for each lubricant coating film, and the average value was used as the indicator of the wear resistance of the lubricant coating film.

(Thermal Resistance)

5% mass loss temperature data were acquired using TG-DTA2000SR available from NETZSCH.

The temperature was increased within the range of 40° C. to 600° C. at a rate of 10° C. per minute at atmospheric pressure, and the temperature at which the mass of the sample was reduced by 5% was measured twice each, and the average thereof was used as an indicator of the thermal resistance.

Synthesis Example 1

[6,6]-diphenyl-C62-bis(butyric acid methyl ester) (bis[60]PCBM, isomer mixture) (1 g, 0.91 mmol) which was a fullerene derivative, Fomblin (registered trademark) TX (average molecular weight: 2,000, 18.2 g, 9.1 mmol) which was a PFPE compound manufactured by Solvay and p-toluenesulfonic acid monohydrate (0.38 g, 2.0 mmol) were added to hexafluorobenzene (100 mL). The mixture was heated to reflux with stirring for 72 hours under a nitrogen stream, thereby allowing the reaction in the above equation to proceed. After the reaction, the reaction mixture was sequentially separated and washed with 0.1 M of aqueous ammonia and pure water. Thereafter, hexafluorobenzene was distilled off from the reaction mixture to obtain a crude product.

Then, the crude product was placed in a thick stainless steel container (inner diameter of 20 mm×depth of 200 mm) having an inlet and an outlet. While maintaining the temperature inside the container at 60° C., supercritical carbon dioxide was caused to flow at a flow rate of 15 mL/min in terms of liquefied carbon dioxide by using a supercritical carbon dioxide feed pump (PU2086-CO2, manufactured by JASCO Corporation). The pressure inside the container was changed in the range of 15 to 22 MPa, and the unreacted Fomblin TX was removed by extraction, thereby obtaining 1.5 g of a brown solid residue. The residue was confirmed to be the reaction product of the above formula (3) (compound 1) from the results of NMR analysis shown below.

$^1$H-NMR (solvent: $CDCl_3$) δ (ppm): 1.8 to 3.3 (12H), 3.6 to 4.0 (20H), 4.1 to 4.4 (4H), 7.3 to 8.3 (10H).

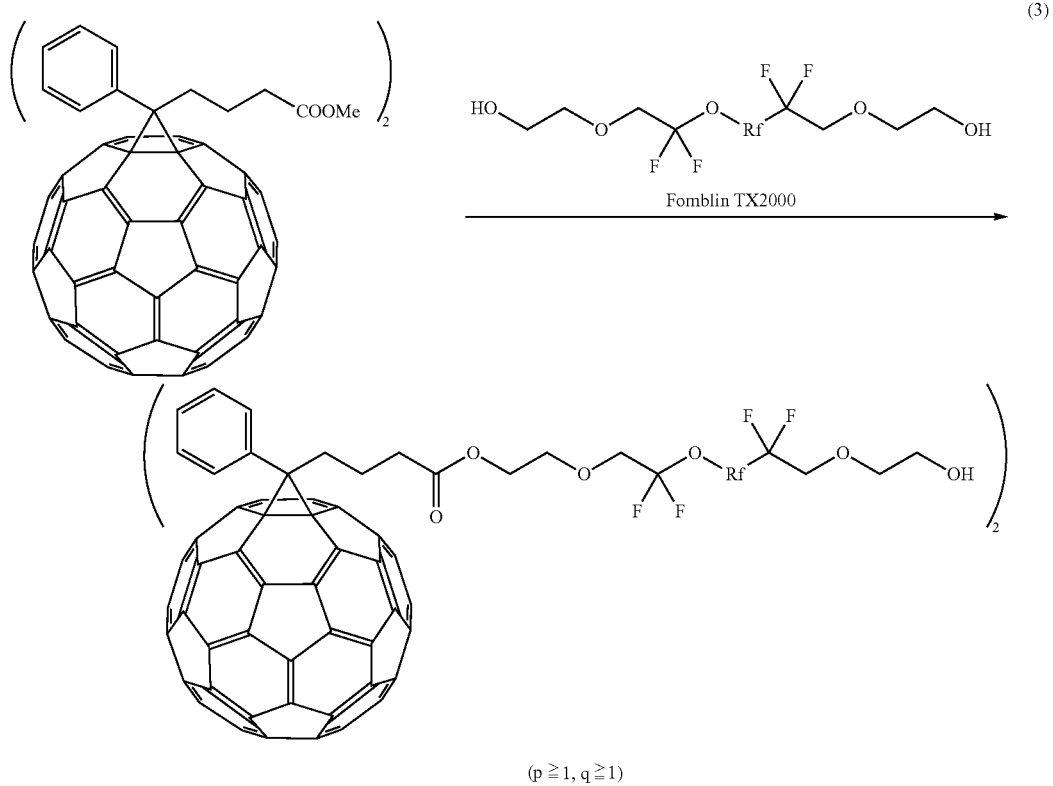

$^{13}$C-NMR (solvent: $CDCl_3$) δ (ppm): 22.8, 34.3, 62.2, 63.6, 64.0, 69.4 to 71.2, 72.7, 73.1, 74.7, 111.7 to 121.4, 128.4 to 129.0, 132.6.

Synthesis Example 2

The PFPE compound as the raw material was changed from Fomblin TX to Fomblin Z-DOL (average molecular weight: 2,000, 18.2 g, 9.1 mmol) manufactured by Solvay. Apart from that, the same operation as in Synthesis Example 1 was carried out to obtain a compound 2 (1.5 g) as a brown solid. The compound 2 is represented as a reaction product in the following reaction formula (4). It is the same as the compound 1 with the exception that the PFPE chain in the molecule is one that reflects the PFPE compound used as a raw material.

Synthesis Example 3

The PFPE compound as the raw material was changed from Fomblin TX to DOH (average molecular weight: 2,000, 18.2 g, 9.1 mmol) manufactured by Daikin Industries, Ltd. Apart from that, the same operation as in Synthesis Example 1 was carried out to obtain a compound 3 (1.5 g) as a brown solid. The compound 3 is a reaction product represented by the following reaction formula (5). It is the same as the compound 1 with the exception that the PFPE chain in the molecule is one that reflects the PFPE compound used as a raw material.

(4)

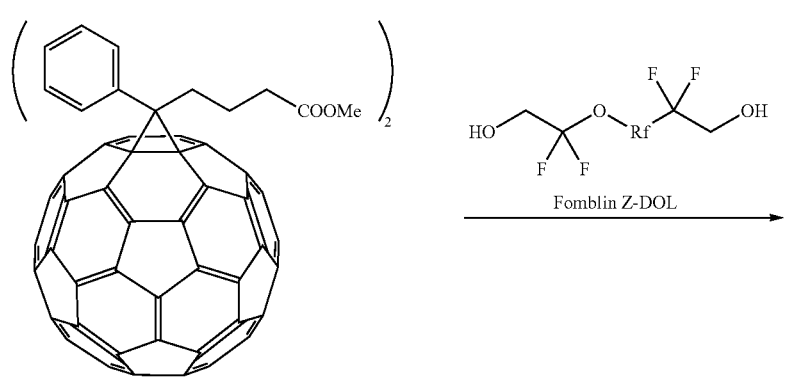

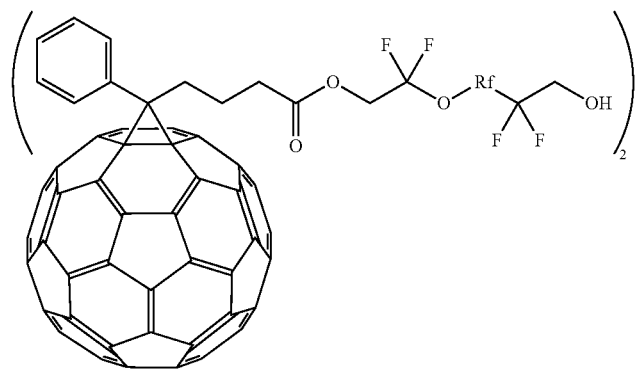

($p \geq 1, q \geq 1$)

$Rf = (CF_2CF_2O)_p(CF_2O)_q$ (5)

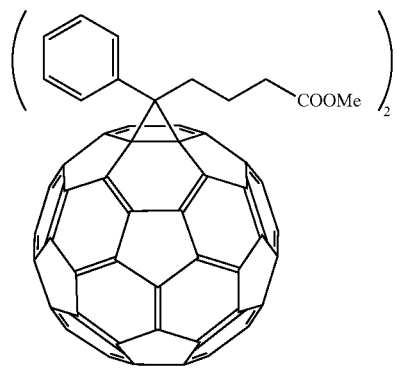 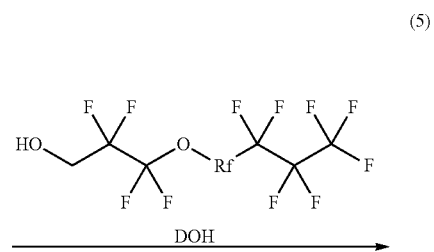

$\xrightarrow{\text{DOH}}$

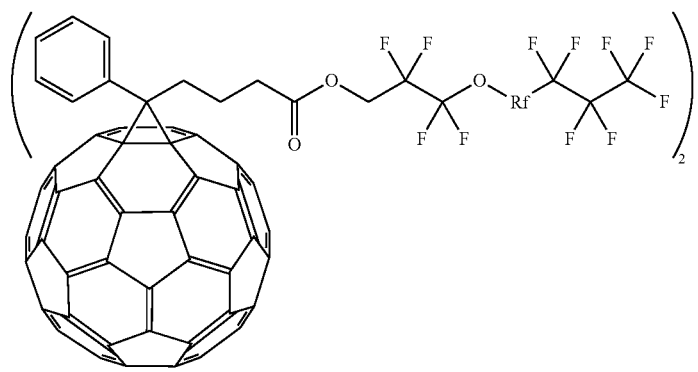

$(x \geq 1)$

Rf = $(CF_2CF_2CF_2O)_x$

Synthesis Example 4

The fullerene derivative as the raw material was changed to [6,6]-phenyl-C63-tris(butyric acid methyl ester) (tris[60] PCBM, isomer mixture) (0.5 g, 0.39 mmol), and the PFPE compound was changed from Fomblin TX to Fomblin Z-DOL (average molecular weight: 2,000, 23.2 g, 11.2 mmol) manufactured by Solvay. Apart from that, the same operation as in Synthesis Example 1 was carried out to obtain a compound 4 (2.1 g) as a brown solid. The compound 4 is a reaction product represented by the following reaction formula (6). It is the same as the compound 1 with the exceptions that the number of the PFPE chains in the molecule is 3, and that the PFPE chains in the molecule are those that reflect the PFPE compound used as a raw material.

(6)

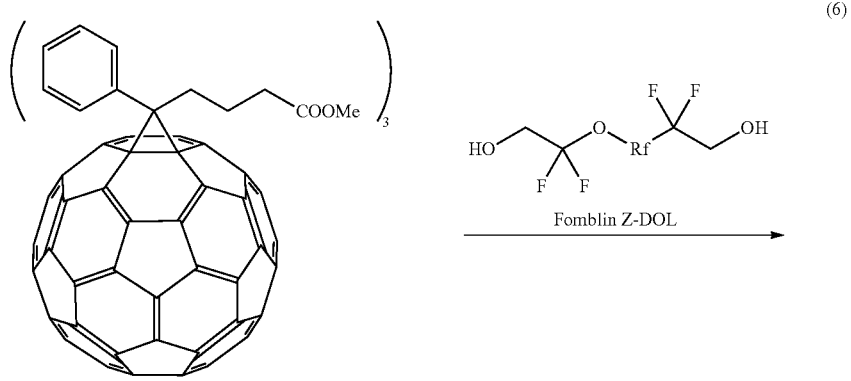

$\xrightarrow{\text{Fomblin Z-DOL}}$

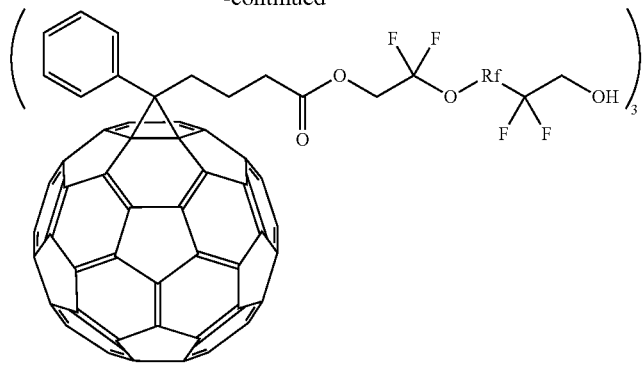

(p ≧ 1, q ≧ 1)

Rf = (CF$_2$CF$_2$O)$_p$(CF$_2$O)$_q$

Synthesis Example 5

The fullerene derivative as the raw material was changed to a mixture of [6,6]-phenyl-C63-tris(butyric acid methyl ester), [6,6]-phenyl-C64-tetrakis(butyric acid methyl ester) and [6,6]-phenyl-C65-pentakis(butyric acid methyl ester) (average addition number n=4, 0.5 g, 0.34 mmol), and the PFPE compound was changed from Fomblin TX to Fomblin Z-DOL (average molecular weight: 2,000, 13.5 g, 6.8 mmol) manufactured by Solvay. Apart from that, the same operation as in Synthesis Example 1 was carried out to obtain a compound 5 (2.5 g) as a brown solid. The compound 5 is a reaction product represented by the following reaction formula (7). It is the same as the compound 1 with the exceptions that the number of the PFPE chains in the molecule is 3 to 5, and that the PFPE chains in the molecule are those that reflect the PFPE compound used as a raw material.

(7)

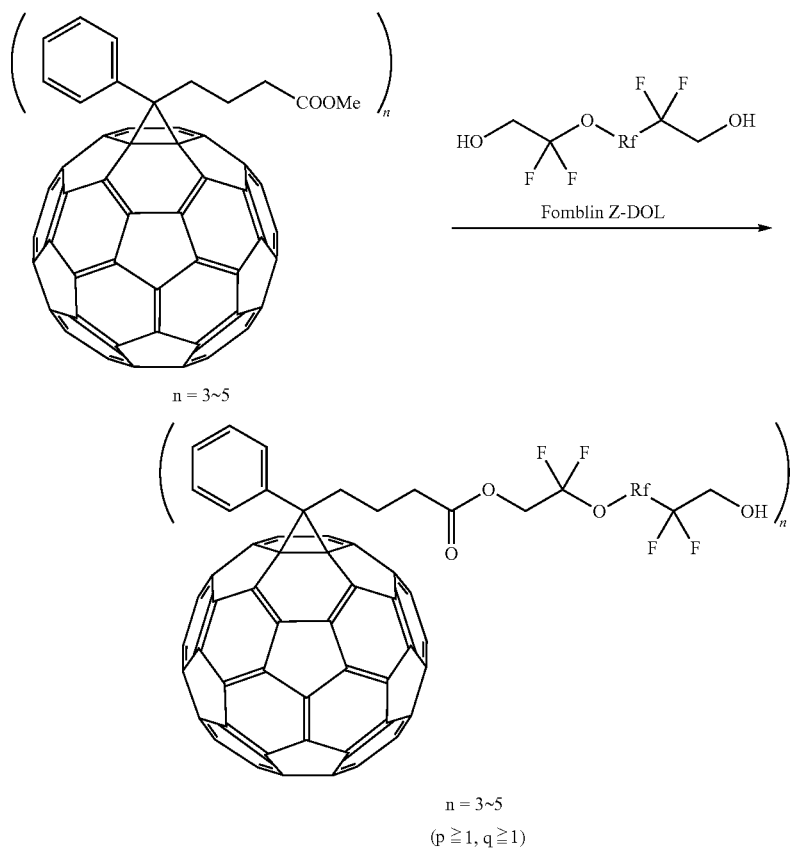

n = 3~5
(p ≧ 1, q ≧ 1)

Rf = (CF$_2$CF$_2$O)$_p$(CF$_2$O)$_q$

Synthesis Example 6

The fullerene derivative as the raw material was changed to [6,6]-phenyl-C61-butyric acid methyl ester ([60]PCBM) (0.83 g, 0.91 mmol), and the PFPE compound was changed from Fomblin TX to Fomblin Z-DOL (average molecular weight: 2,000, 18.2 g, 9.1 mmol) manufactured by Solvay. Apart from that, the same operation as in Synthesis Example 1 was carried out to obtain a compound 6 (1.2 g) as a brown solid. The compound 6 is a reaction product represented by the following reaction formula (8). It is the same as the compound 1 with the exceptions that the number of the PFPE chains in the molecule is one, and that the PFPE chain in the molecule is one that reflects the PFPE compound used as a raw material.

Synthesis Example 7

The fullerene derivative as the raw material was changed to a compound 7A of general formula (9) (1.00 g, 1.00 mmol), and the PFPE compound was changed from Fomblin TX to Fomblin Z-DOL (average molecular weight: 2,000, 20.0 g, 10 mmol) manufactured by Solvay. Apart from that, the same operation as in Synthesis Example 1 was carried out to obtain a compound 7 (1.8 g) as a brown solid.

(8)

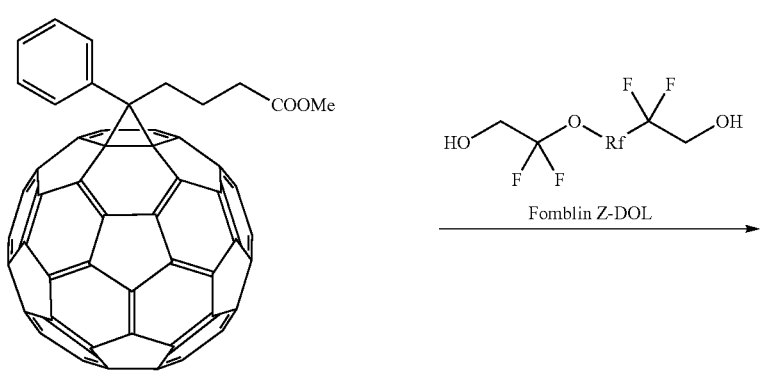

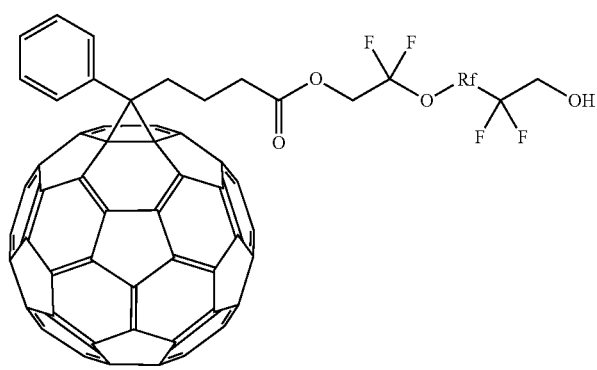

$(p \geq 1, q \geq 1)$ $Rf = (CF_2CF_2O)_p(CF_2O)_q$

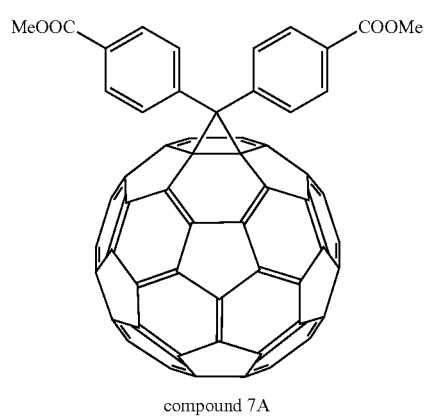

compound 7A

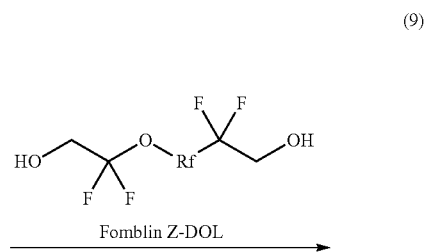

Fomblin Z-DOL (9)

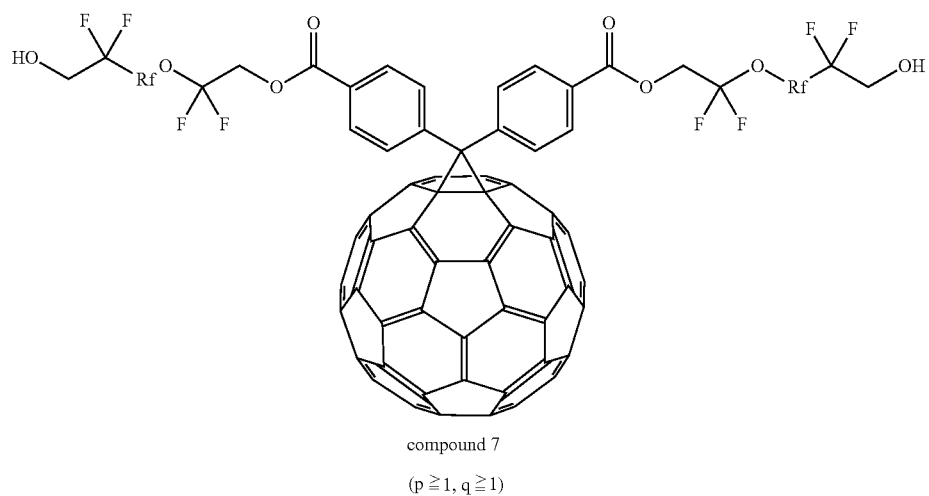

compound 7
(p ≧ 1, q ≧ 1)

Rf = (CF$_2$CF$_2$O)$_p$(CF$_2$O)$_q$

Synthesis Example 8

The fullerene derivative as the raw material was changed to a compound 8A of general formula (10) (1.07 g, 1.00 mmol), and the PFPE compound was changed from Fomblin TX to Fomblin Z-DOL (average molecular weight: 2,000, 30.0 g, 15 mmol) manufactured by Solvay. Apart from that, the same operation as in Synthesis Example 1 was carried out to obtain a compound 8 (2.7 g) as a brown solid.

(10)

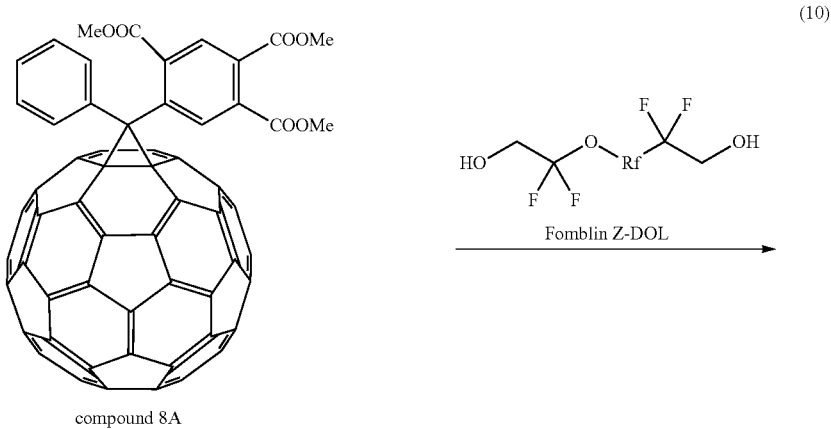

compound 8A

Fomblin Z-DOL

-continued

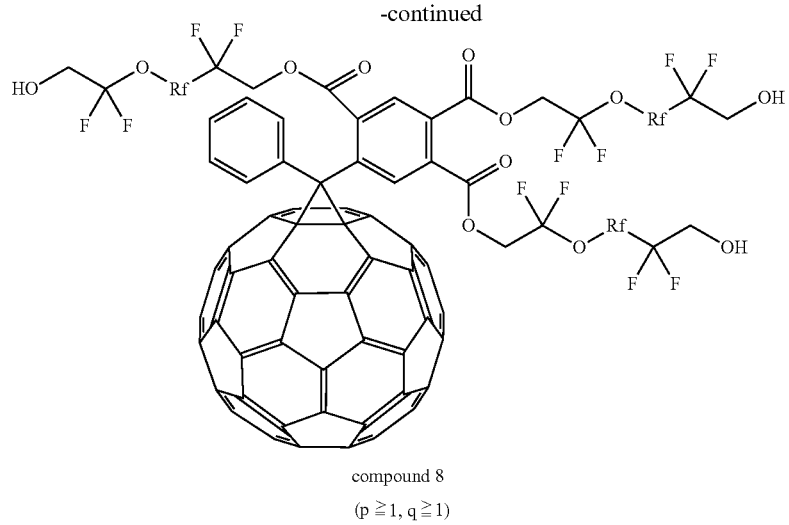

compound 8
(p ≧ 1, q ≧ 1)

Rf = (CF$_2$CF$_2$O)$_p$(CF$_2$O)$_q$

Synthesis Example 9

The fullerene derivative as the raw material was changed to a compound 9A of general formula (11) (1.12 g, 1.00 mmol), and the PFPE compound was changed from Fomblin TX to Fomblin Z-DOL (average molecular weight: 2,000, 40.0 g, 20 mmol) manufactured by Solvay. Apart from that, the same operation as in Synthesis Example 1 was carried out to obtain a compound 9 (3.4 g) as a brown solid.

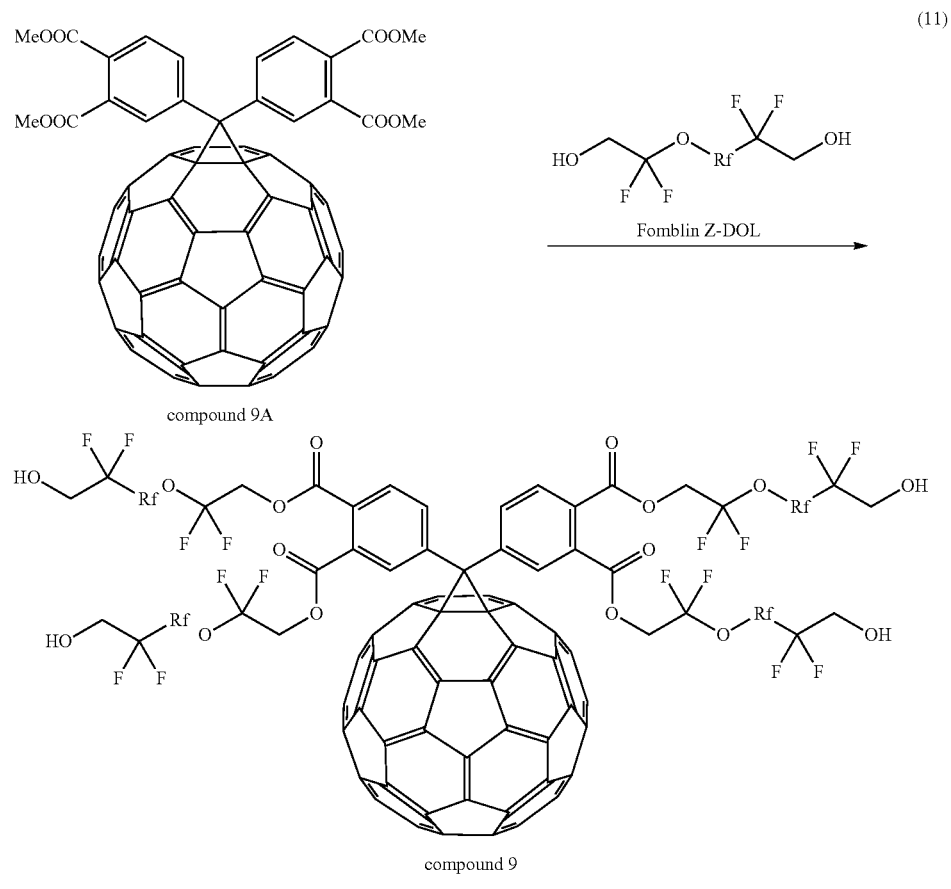

(11)

compound 9
(p ≧ 1, q ≧ 1)

Rf = (CF$_2$CF$_2$O)$_p$(CF$_2$O)$_q$

Synthesis Example 10

The fullerene derivative as the raw material was changed to a compound 10A of general formula (12) (1.23 g, 1.00 mmol), and the PFPE compound was changed from Fomblin TX to Fomblin Z-DOL (average molecular weight: 2,000, 20.0 g, 10 mmol) manufactured by Solvay. Apart from that, the same operation as in Synthesis Example 1 was carried out to obtain a compound 10 (1.6 g) as a brown solid.

Synthesis Example 12

The fullerene derivative as the raw material was changed to a compound 11A of general formula (13) (0.85 g, 1.00 mmol), and the PFPE compound was changed from Fomblin TX to Fomblin Z-DOL (average molecular weight: 2,000, 20.0 g, 10 mmol) manufactured by Solvay. Apart from that, the same operation as in Synthesis Example 1 was carried out to obtain a compound 11 (1.5 g) as a brown solid.

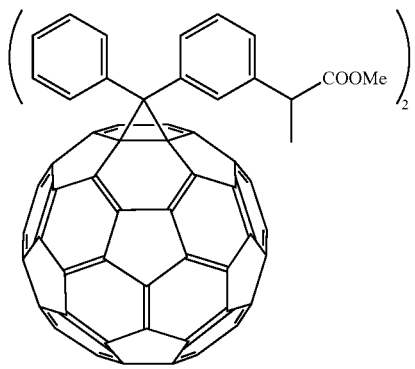

compound 10A

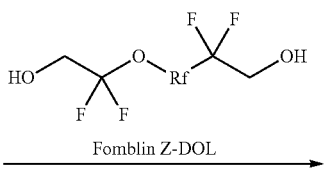

Fomblin Z-DOL

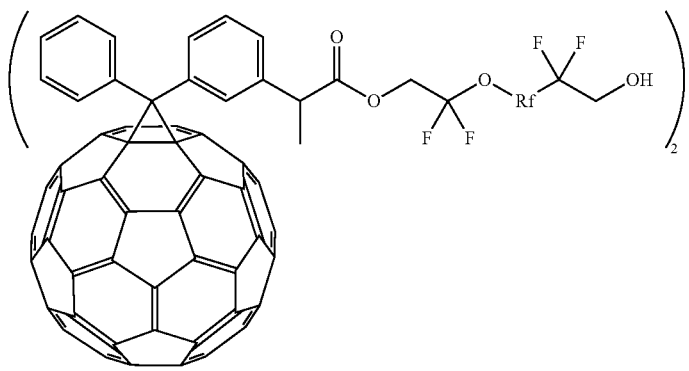

compound 10

($p \geq 1$, $q \geq 1$)

$Rf = (CF_2CF_2O)_p(CF_2O)_q$

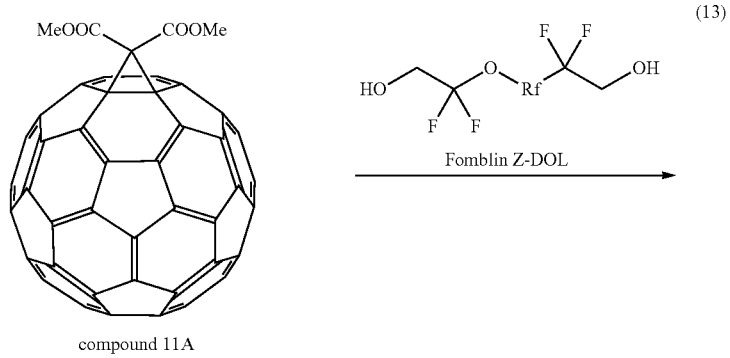
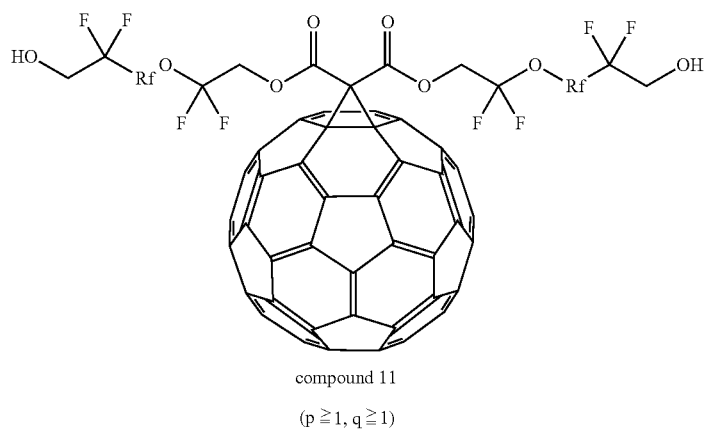
Synthesis Example 12
The fullerene derivative as the raw material was changed to a compound 12A of general formula (14) (0.98 g, 1.00 mmol), and the PFPE compound was changed from Fomblin TX to Fomblin Z-DOL (average molecular weight: 2,000, 40.0 g, 20 mmol) manufactured by Solvay. Apart from that, the same operation as in Synthesis Example 1 was carried out to obtain a compound 12 (3.1 g) as a brown solid.
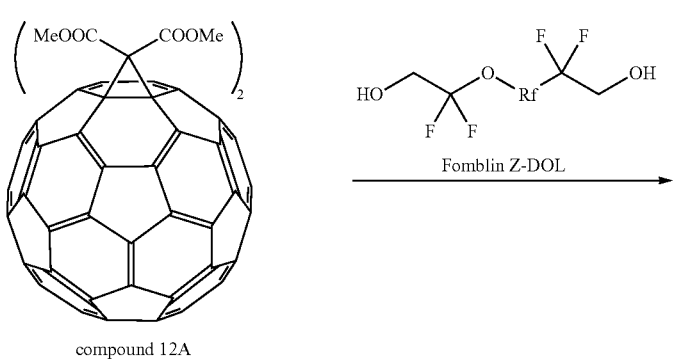

-continued

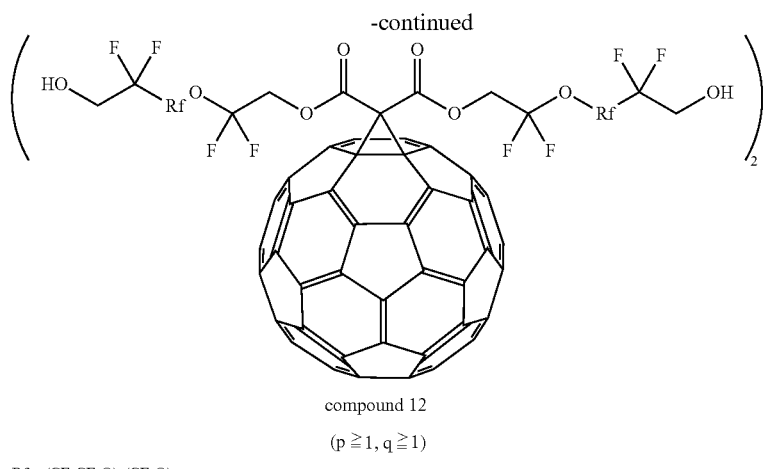

compound 12

(p ≧ 1, q ≧ 1)

Rf = (CF$_2$CF$_2$O)$_p$(CF$_2$O)$_q$

Example 1

A carbon protective film was formed by depositing diamond like carbon (DLC) onto a 2.5 inch glass blank for a magnetic disk by high-frequency magnetron sputtering in an Ar gas atmosphere using carbon as a target to produce a simulated disk.

Then, using the compound 1 obtained in Synthesis Example 1 as a lubricant and D4OH (trade name, manufactured by MORESCO Corporation) as a PFPE compound, they were mixed so that the mass ratio thereof was 3:7 to prepare a lubricant. The lubricant was dissolved in Vertrel (registered trademark) XF (manufactured by Du Pont-Mitsui Fluorochemicals Co., Ltd.) so that the concentration of the lubricant was 0.012% by mass, thereby preparing a lubricant layer forming solution.

Then, by using a dipping method, the lubricant layer forming solution was applied onto the protective film of the simulated disk by the following method. The simulated disk was immersed in the lubricant layer forming solution in an immersion tank of a dip coater, and then the simulated disk was withdrawn at a constant speed from the immersion tank. Then, the lubricant layer forming solution was applied on the surface of the protective film of the simulated disk.

Thereafter, a lubricant layer was formed by drying the surface where the lubricant layer forming solution was applied. The average film thickness and the frictional sliding test result of the lubricant layer obtained in this manner are shown in Table 1.

Examples 2 to 15

The compounds used as lubricants and the ratios thereof were changed as shown in Table 1. Apart from that, a lubricant coating film was formed on the surface of the simulated disk in the same manner as in Example 1, and was evaluated in the same manner as in Example 1. The results are shown in Table 1.

Comparative Example 1

D4OH alone was used as a lubricant. Apart from that, a lubricant coating film was formed on the surface of the simulated disk in the same manner as in Example 1, and was evaluated in the same manner as in Example 1. The results are shown in Table 1.

Comparative Example 2

In place of the compound 1 as a lubricant, A20H (trade name, manufactured by MORESCO Corporation) was used which was a PFPE compound. Apart from that, a lubricant coating film was formed on the surface of the simulated disk in the same manner as in Example 1, and was evaluated in the same manner as in Example 1. The results are shown in Table 1.

Comparative Example 3

In place of the compound 1 as a lubricant, a compound 6 was used which was a compound after the reaction in the general formula (8). Apart from that, a lubricant coating film was formed on the surface of the simulated disk in the same manner as in Example 1. Because the fullerene compound had precipitated on the simulated disk, it was not possible to evaluate the wear resistance.

Comparative Example 4

In place of the compound 1 as a lubricant, a fullerene compound described in Patent Document 3 (Japanese Unexamined Patent Application, First Publication No. 2013-170137) and represented by the following formula (15) was used. Apart from that, a lubricant coating film was formed on the surface of the simulated disk in the same manner as in Example 1. Because the fullerene compound had precipitated on the simulated disk, it was not possible to evaluate the wear resistance.

(15)

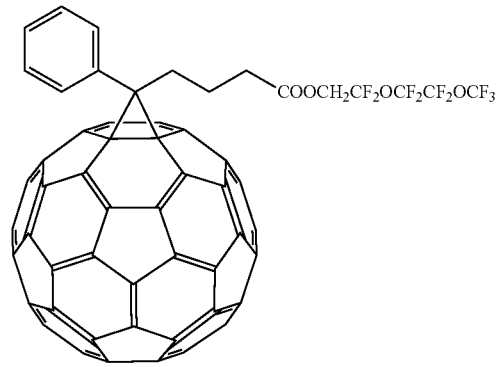

Comparative Example 5

In place of the compound 1 as a lubricant, a fullerene C60 was used, and a mixed organic solvent of isopropyl alcohol and toluene (mass ratio 1:1) was used in place of Vertrel XF as a coating solvent. Apart from that, a lubricant coating film was formed on the surface of the simulated disk in the same manner as in Example 1. Because the fullerene C60 had precipitated on the simulated disk, it was not possible to evaluate the wear resistance.

Comparative Example 6

In place of the compound 1 as a lubricant, a compound with a carboxyl group described in Patent Document 1 (Japanese Unexamined Patent Application, First Publication No. 2006-131874) and represented by the following formula (16) was used, and a mixed organic solvent of isopropyl alcohol and toluene (mass ratio 1:1) was used in place of Vertrel XF as a coating solvent. Apart from that, a lubricant coating film was formed on the surface of the simulated disk in the same manner as in Example 1. Because the fullerene compound had precipitated on the simulated disk, it was not possible to evaluate the wear resistance.

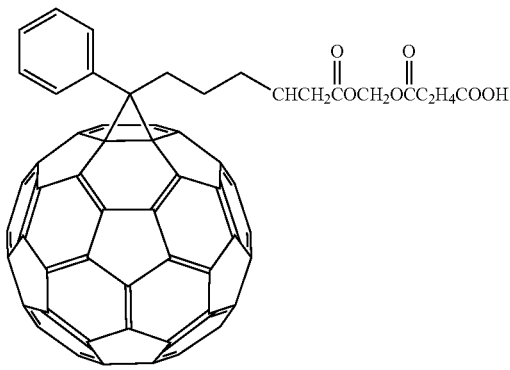

(16)

Comparative Example 7

In place of the compound 1 as a lubricant, a hydroxylated fullerene (C60-(OH)10) described in Patent Document 1 (Japanese Unexamined Patent Application, First Publication No. 2006-131874) was used, and a mixed organic solvent of isopropyl alcohol and toluene (mass ratio 1:1) was used in place of Vertrel XF as a coating solvent. Apart from that, a lubricant coating film was formed on the surface of the simulated disk in the same manner as in Example 1. Because the hydroxylated fullerene had precipitated on the simulated disk, it was not possible to evaluate the wear resistance.

TABLE 1

|  | Lubricant (mass ratio) | Average film thickness (nm) | Time until the friction coefficient varied (sec) |
|---|---|---|---|
| Example 1 | Compound 1/D4OH (3/7) | 1.5 | 630 |
| Example 2 | Compound 2/D4OH (3/7) | 1.6 | 710 |

TABLE 1-continued

|  | Lubricant (mass ratio) | Average film thickness (nm) | Time until the friction coefficient varied (sec) |
|---|---|---|---|
| Example 3 | Compound 3/D4OH (3/7) | 1.5 | 590 |
| Example 4 | Compound 4/D4OH (3/7) | 1.5 | 700 |
| Example 5 | Compound 5/D4OH (3/7) | 1.6 | 670 |
| Example 6 | Compound 7/D4OH (3/7) | 1.5 | 690 |
| Example 7 | Compound 8/D4OH (3/7) | 1.4 | 630 |
| Example 8 | Compound 9/D4OH (3/7) | 1.4 | 660 |
| Example 9 | Compound 10/D4OH (3/7) | 1.6 | 700 |
| Example 10 | Compound 11/D4OH (3/7) | 1.3 | 630 |
| Example 11 | Compound 12/D4OH (3/7) | 1.5 | 690 |
| Example 12 | Compound 2/D4OH (1/7) | 1.4 | 580 |
| Example 13 | Only compound 2 | 1.7 | 600 |
| Example 14 | Only compound 7 | 1.4 | 670 |
| Example 15 | Only compound 11 | 1.6 | 620 |
| Comparative Example 1 | Only D4OH | 1.5 | 530 |
| Comparative Example 2 | A20H/D4OH (3/7) | 1.4 | 400 |

As a result, it is clear that the time until the friction coefficient increased was longer and the wear resistance was higher in Examples 1 to 15, as compared to Comparative Examples 1 and 2.

Example 16

300 mg of perfluoroelastomer (DAI-EL Perfluoro GA-65 manufactured by Daikin Industries, Ltd.) was swollen and dissolved in 5 mL of hydrofluorocarbon as a fluorine-based solvent (ASAHIKLIN AC-2000, manufactured by Asahi Glass Co., Ltd.). 3 mg of the compound 1 was added to this mixture, and after stirring the resulting mixture for 1 day, the solvent was removed by evaporation and the resultant was subjected to vacuum drying for 12 hours at 50° C. As a result, a perfluoroelastomer composition containing 1% by mass of the compound 1 with respect to perfluoroelastomer was obtained. The 5% mass loss temperature of the resulting composition is shown in Table 2.

Examples 17 to 29

The compound 1 as a fullerene derivative and the added amount thereof were changed to the compound and amount described in Table 2. Apart from that, a perfluoroelastomer composition was prepared in the same manner as in Example 16, and was evaluated in the same manner as in Example 16. The 5% mass loss temperature of the resulting composition is shown in Table 2.

Comparative Example 8

Only the perfluoroelastomer used in Example 16 was evaluated in the same manner as in Example 16. These results are shown in Table 2.

Comparative Example 9

Using the compound 6 instead of the compound 1 used in Example 16, operations were carried out in the same manner as in Example 16. Since the perfluoroelastomer and the compound 6 were separated in the resultant obtained after drying, the subsequent evaluation was not conducted.

TABLE 2

|  | Compound | Added amount | 5% mass loss temperature |
|---|---|---|---|
| Example 16 | Compound 1 | 1% | 438° C. |
| Example 17 | Compound 2 | 1% | 439° C. |
| Example 18 | Compound 3 | 1% | 436° C. |
| Example 19 | Compound 4 | 1% | 433° C. |
| Example 20 | Compound 5 | 1% | 432° C. |
| Example 21 | Compound 7 | 1% | 440° C. |
| Example 22 | Compound 8 | 1% | 437° C. |
| Example 23 | Compound 9 | 1% | 433° C. |
| Example 24 | Compound 10 | 1% | 438° C. |
| Example 25 | Compound 11 | 1% | 434° C. |
| Example 26 | Compound 12 | 1% | 431° C. |
| Example 27 | Compound 2 | 0.10% | 430° C. |
| Example 28 | Compound 10 | 0.10% | 430° C. |
| Example 29 | Compound 11 | 0.10% | 429° C. |
| Comparative Example 8 | None | — | 424° C. |

As a result, the 5% mass loss temperatures were higher in Examples 16 to 29 as compared to Comparative Example 8, thereby demonstrating that the fullerene derivatives of the present invention have an effect of improving the thermal resistance of the fluororesin.

INDUSTRIAL APPLICABILITY

By being incorporated in a lubricant, the fullerene derivative of the present invention is effective in improving the wear resistance of the lubricant. In addition, by being incorporated in a fluororesin, the fullerene derivative of the present invention is effective in improving the thermal resistance of the fluororesin.

The invention claimed is:
1. A fullerene derivative comprising, in a molecule,
a fullerene skeleton; and
a plurality of perfluoropolyether chains linked to the fullerene skeleton via a carbon atom bonded to the fullerene skeleton at two locations,
wherein the fullerene derivative is a compound represented by the following general formula (1):

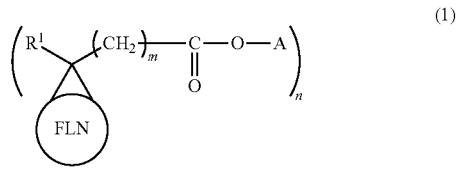

wherein FLN represents a fullerene skeleton, A represents a group having a perfluoropolyether chain, $R^1$ represents an aryl group having at most 24 carbon atoms, m is an integer of 0 to 5, and n is an integer of 2 to 5.

2. The fullerene derivative according to claim 1, comprising 2 to 5 perfluoropolyether chains linked to the fullerene skeleton.

3. The fullerene derivative according to claim 1, wherein the fullerene skeleton is C60.

4. The fullerene derivative according to claim 1,
wherein the perfluoroether chains have at least one partial structure selected from the group consisting of $-(CF_2O)_x-$, $-(CF_2CF_2O)_x-$, $-(CF_2CF_2CF_2O)_x-$, $-(CF_2CF_2CF_2CF_2O)_x-$, and $-(CF_2(CF_2)_3CF_2O)_x-$:
(with the proviso that in the formula, x is an integer of 1 to 50).

5. The fullerene derivative according to claim 1,
wherein the perfluoroether chains have a partial structure represented by $-(CF_2CF_2O)_y(CF_2O)_z-$:
(with the proviso that in the formula, y and z are integers of 1 to 50).

6. A fluororesin composition comprising the fullerene derivative according to claim 1.

7. A lubricant comprising the fullerene derivative according to claim 1.

8. The lubricant according to claim 7, further comprising a perfluoropolyether compound having no fullerene skeleton.

* * * * *